US009873764B2

(12) United States Patent
Mihov et al.

(10) Patent No.: US 9,873,764 B2
(45) Date of Patent: *Jan. 23, 2018

(54) PARTICLES COMPRISING POLYESTERAMIDE COPOLYMERS FOR DRUG DELIVERY

(75) Inventors: George Mihov, Echt (NL); John Andrew Zupancich, Echt (NL)

(73) Assignee: DSM IP ASSETS, B.V., Heerlen (NL)

( * ) Notice: Subject to any disclaimer, the term of this patent is extended or adjusted under 35 U.S.C. 154(b) by 499 days.

This patent is subject to a terminal disclaimer.

(21) Appl. No.: 14/128,731

(22) PCT Filed: Jun. 25, 2012

(86) PCT No.: PCT/EP2012/062267
§ 371 (c)(1),
(2), (4) Date: Dec. 23, 2013

(87) PCT Pub. No.: WO2012/175748
PCT Pub. Date: Dec. 27, 2012

(65) Prior Publication Data
US 2014/0120170 A1    May 1, 2014

(30) Foreign Application Priority Data

Jun. 23, 2011    (EP) .................................. 11171191

(51) Int. Cl.
*A61K 47/34*    (2017.01)
*C08G 69/44*    (2006.01)
(Continued)

(52) U.S. Cl.
CPC ............ *C08G 69/44* (2013.01); *A61K 31/165* (2013.01); *A61K 47/34* (2013.01);
(Continued)

(58) Field of Classification Search
None
See application file for complete search history.

(56) References Cited

U.S. PATENT DOCUMENTS 4,129,594 A    12/1978    Baker et al.
4,221,787 A    9/1980    Bodor et al.
(Continued)

FOREIGN PATENT DOCUMENTS

AU    2001287015    3/2002
AU    2006204654    9/2006
(Continued)

OTHER PUBLICATIONS

Algebraic Properties [Axioms], p. 1, 2009 Mathematics Standards of Learning, Virginia Department of Education, Fall 2012; accessed as http://www.doe.virginia.gov/instruction/mathematics/resources/va_algebraic_properties.pdf, on Aug. 7, 2017.*
(Continued)

*Primary Examiner* — Bethany P Barham
*Assistant Examiner* — Dominic Lazaro
(74) *Attorney, Agent, or Firm* — Kevin M. Bull

(57) ABSTRACT

The present disclosure relates to microparticles or nanoparticles comprising a polyesteramide (PEA) having a chemical formula described by structural formula (IV), $$\left\{\left[\begin{array}{c}\overset{O}{\underset{\|}{C}}-R_1-\overset{O}{\underset{\|}{C}}-\underset{\underset{H}{|}}{N}-\underset{\underset{R_3}{|}}{C}-\overset{O}{\underset{\|}{C}}-O-R_5-O-\overset{O}{\underset{\|}{C}}-\underset{\underset{R_3}{|}}{C}-\underset{\underset{H}{|}}{N}\end{array}\right]_m\right.$$

Figure 1:
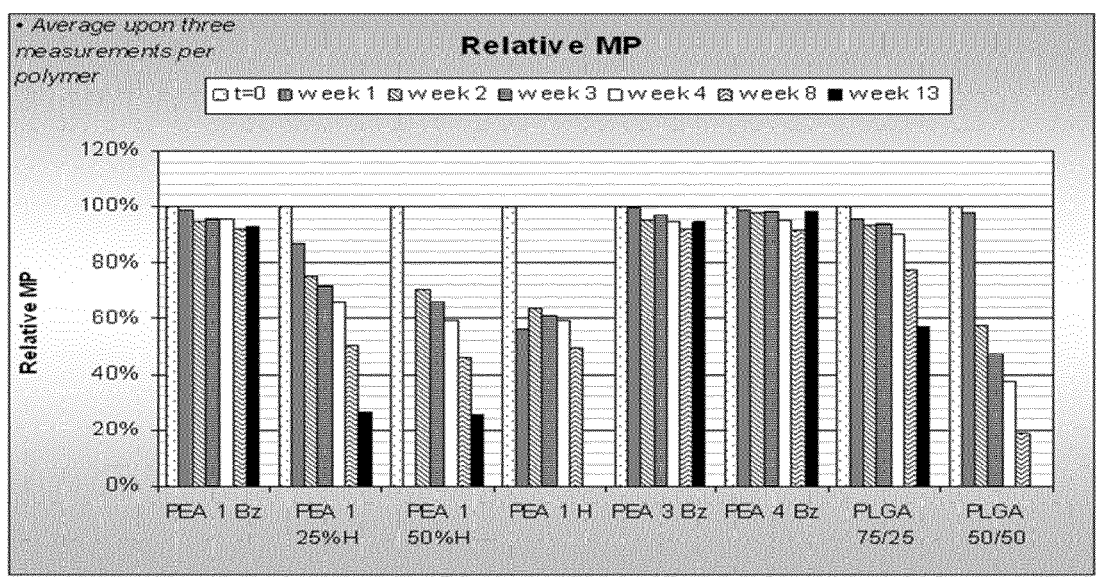

$$\left.\left[\begin{array}{c}\overset{O}{\underset{\|}{C}}-R_1-\overset{O}{\underset{\|}{C}}-\underset{\underset{H}{|}}{N}-\underset{\underset{R_4}{|}}{C}-\overset{O}{\underset{\|}{C}}-O-R_6-O-\overset{O}{\underset{\|}{C}}-\underset{\underset{R_4}{|}}{C}-\underset{\underset{H}{|}}{N}\end{array}\right]_p\right.$$

Formula (IV)

(Continued)

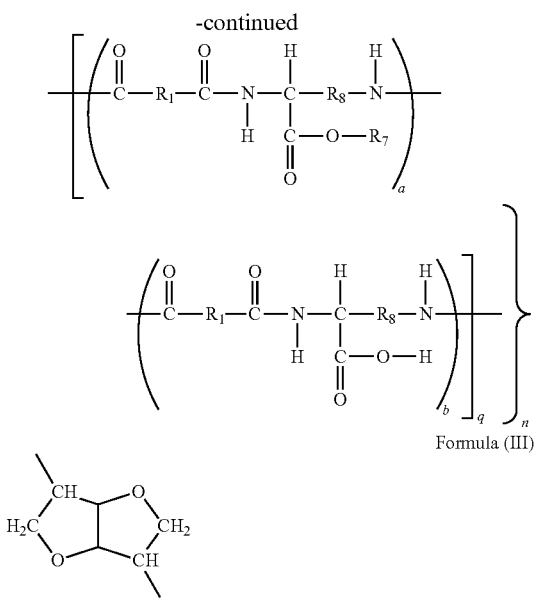

Formula (III)

wherein m+p varies from 0.9-0.1 and q varies from 0.1 to 0.9; m+p+q=1 whereby m or p could be 0; n is about 5 to about 300; (pref. 50-200); $R_1$ is independently selected from the group consisting of ($C_2$-$C_{20}$) alkylene, ($C_2$-$C_{20}$) alkenylene, —($R_9$—CO—O—$R_{10}$—O—CO—$R_9$)—, —CH$R_{11}$—O—CO—$R_{12}$—COOC$R_{11}$— and combinations thereof; $R_3$ and $R_4$ in a single backbone unit m or p, respectively, are independently selected from the group consisting of hydrogen, ($C_1$-$C_6$)alkyl, ($C_2$-$C_6$)alkenyl, ($C_2$-$C_6$)alkynyl, ($C_6$-$C_{10}$)aryl, ($C_1$-$C_6$)alkyl, —(CH$_2$)SH, —(CH$_2$)$_2$S(CH$_3$), —CH$_2$OH, —CH(OH)CH$_3$, —(CH$_2$)$_4$NH$_3$+, —(CH$_2$)$_3$NHC(=NH$_2$+)NH$_2$, —CH$_2$COOH, —(CH$_2$)COOH, —CH$_2$—CO—NH$_2$, —CH$_2$CH$_2$—CO—NH$_2$, —CH$_2$CH$_2$COOH, CH$_3$—CH$_2$—CH(CH$_3$)—, (CH$_3$)$_2$—CH—CH$_2$—, H$_2$N—(CH$_2$)$_4$—, Ph-CH$_2$—, CH=C—CH$_2$—, HO-p-Ph-CH$_2$—, (CH$_3$)$_2$—CH—, Ph-NH—, NH—(CH$_2$)$_3$—C—, NH—CH=N—CH=C—CH$_2$—; $R_5$ is selected from the group consisting of ($C_2$-$C_{20}$)alkylene, ($C_2$-$C_{20}$)alkenylene, alkyloxy or oligoethyleneglycol; $R_6$ is selected from bicyclic-fragments of 1,4:3,6-dianhydrohexitols of structural formula (III); $R_7$ is ($C_6$-$C_{10}$)aryl ($C_1$-$C_6$)alkyl; $R_8$ is —(CH$_2$)$_4$—; $R_9$ or $R_{10}$ are independently selected from $C_2$-$C_{12}$ alkylene or $C_2$-$C_{12}$ alkenylene; and $R_{11}$ or $R_{12}$ are independently selected from H, methyl, $C_2$-$C_{12}$ alkylene or $C_2$-$C_{12}$ alkenylene; whereby a is at least 0.05 and b is at least 0.05 and a+b=1.

20 Claims, 3 Drawing Sheets

(51) Int. Cl.
  *A61K 47/69* (2017.01)
  *C08L 77/12* (2006.01)
  *C08J 5/18* (2006.01)
  *A61K 31/165* (2006.01)
(52) U.S. Cl.
  CPC ............ *A61K 47/6921* (2017.08); *C08J 5/18* (2013.01); *C08L 77/12* (2013.01); *C08J 2377/12* (2013.01); *Y10T 428/2982* (2015.01)

(56) References Cited

U.S. PATENT DOCUMENTS

| | | |
|---|---|---|
| 4,443,563 A | 4/1984 | Dirlikov et al. |
| 4,550,730 A | 11/1985 | Shalaby et al. |
| 4,994,551 A | 2/1991 | Fung et al. |
| 5,057,313 A | 10/1991 | Shih et al. |
| 5,091,560 A | 2/1992 | Rowland |
| 5,100,992 A | 3/1992 | Cohn et al. |
| 5,133,742 A | 7/1992 | Pinchuk |
| 5,206,341 A | 4/1993 | Ibay et al. |
| 5,286,837 A | 2/1994 | Barrows et al. |
| 5,300,114 A | 4/1994 | Gwon et al. |
| 5,449,513 A | 9/1995 | Yokoyama et al. |
| 5,482,700 A | 1/1996 | Deutsch et al. |
| 5,485,496 A | 1/1996 | Lee et al. |
| 5,514,379 A | 5/1996 | Weissleder et al. |
| 5,516,881 A | 5/1996 | Lee et al. |
| 5,554,692 A | 9/1996 | Ross |
| 5,583,206 A | 12/1996 | Snow et al. |
| 5,591,227 A | 1/1997 | Dinh et al. |
| 5,610,241 A | 3/1997 | Lee et al. |
| 5,653,998 A | 8/1997 | Hamann et al. |
| 5,721,131 A | 2/1998 | Rudolph et al. |
| 5,753,234 A | 5/1998 | Lee et al. |
| 5,762,939 A | 6/1998 | Smith et al. |
| 5,770,229 A | 6/1998 | Tanihara et al. |
| 5,849,841 A | 12/1998 | Muhlebach et al. |
| 5,852,155 A | 12/1998 | Bussink et al. |
| 5,858,368 A | 1/1999 | Smith et al. |
| 5,861,387 A | 1/1999 | Labrie et al. |
| 5,874,064 A | 2/1999 | Edwards et al. |
| 5,882,679 A | 3/1999 | Needham |
| 5,885,491 A | 3/1999 | Galan Valdivia et al. |
| 5,904,936 A | 5/1999 | Huille et al. |
| 5,906,934 A | 5/1999 | Grande et al. |
| 5,916,585 A | 6/1999 | Cook et al. |
| 5,919,893 A | 7/1999 | Roby et al. |
| 5,968,794 A | 10/1999 | Samain et al. |
| 5,972,027 A | 10/1999 | Johnson |
| 6,004,573 A | 12/1999 | Rathi et al. |
| 6,103,526 A | 8/2000 | Smith et al. |
| 6,111,058 A | 8/2000 | Warzelhan et al. |
| 6,153,252 A | 11/2000 | Hossainy et al. |
| 6,171,610 B1 | 1/2001 | Vacanti et al. |
| 6,210,441 B1 | 4/2001 | Flodin |
| 6,221,997 B1 | 4/2001 | Woodhouse et al. |
| 6,228,391 B1 | 5/2001 | Shimizu et al. |
| 6,245,532 B1 | 6/2001 | Smith et al. |
| 6,299,597 B1 | 10/2001 | Buscemi et al. |
| 6,342,300 B1 | 1/2002 | Bengs et al. |
| 6,352,667 B1 | 3/2002 | English |
| 6,365,160 B1 | 4/2002 | Webb et al. |
| 6,428,807 B1 | 8/2002 | MacFarlan et al. |
| 6,476,204 B1 | 11/2002 | Kim et al. |
| 6,503,538 B1 | 1/2003 | Chu et al. |
| 6,521,431 B1 | 2/2003 | Kiser et al. |
| 6,541,606 B2 | 4/2003 | Margolin et al. |
| 6,660,525 B2 | 12/2003 | Martin et al. |
| 6,703,040 B2 | 3/2004 | Katsarava et al. |
| 6,716,445 B2 | 4/2004 | Won et al. |
| 6,793,938 B2 | 9/2004 | Sankaram |
| 6,830,747 B2 | 12/2004 | Lang et al. |
| 6,982,249 B1 | 1/2006 | Schmaier et al. |
| 6,984,393 B2 | 1/2006 | Amsden |
| 6,994,867 B1 | 2/2006 | Hossainy et al. |
| 7,026,156 B1 | 4/2006 | Clark et al. |
| 7,041,785 B1 | 5/2006 | Recoli et al. |
| 7,122,202 B2 | 10/2006 | Allen et al. |
| 7,220,816 B2 | 5/2007 | Pacetti et al. |
| 7,304,122 B2 | 12/2007 | Chu et al. |
| 7,408,018 B2 | 8/2008 | Chu et al. |
| 7,538,180 B2 | 5/2009 | Pacetti et al. |
| 7,649,022 B2 | 1/2010 | Gomurashvili et al. |
| 7,658,727 B1 | 2/2010 | Fernandes et al. |
| 7,670,829 B2 | 3/2010 | Spagnoli et al. |
| 7,744,861 B2 | 6/2010 | Zhao et al. |
| 7,785,618 B2 | 8/2010 | Elmaleh et al. |

(56) References Cited

U.S. PATENT DOCUMENTS

| | | |
|---|---|---|
| 7,794,494 B2 | 9/2010 | Sahatjian et al. |
| 7,794,706 B2 | 9/2010 | Carpenter et al. |
| 7,863,406 B2 | 1/2011 | Chu et al. |
| 7,935,493 B2 | 5/2011 | Michnick et al. |
| 8,067,031 B2 | 11/2011 | Daniloff et al. |
| 8,163,269 B2 | 4/2012 | Carpenter et al. |
| 2001/0038851 A1 | 11/2001 | Allen et al. |
| 2002/0015720 A1 | 2/2002 | Katsarava et al. |
| 2002/0034532 A1 | 3/2002 | Brodbeck et al. |
| 2002/0044972 A1 | 4/2002 | Davis et al. |
| 2002/0049495 A1 | 4/2002 | Kutryk et al. |
| 2002/0106369 A1 | 8/2002 | Horvath et al. |
| 2002/0147296 A1 | 10/2002 | Teller et al. |
| 2002/0164374 A1 | 11/2002 | Jackson et al. |
| 2002/0165347 A1 | 11/2002 | Fox et al. |
| 2002/0168338 A1 | 11/2002 | Baird |
| 2002/0173586 A1 | 11/2002 | Jeong et al. |
| 2003/0064053 A1 | 4/2003 | Liu et al. |
| 2003/0130185 A1 | 7/2003 | Bar-Or et al. |
| 2003/0175239 A1 | 9/2003 | Margolin et al. |
| 2003/0215454 A1 | 11/2003 | Colb et al. |
| 2003/0217748 A1 | 11/2003 | Giroux |
| 2003/0229393 A1 | 12/2003 | Kutryk et al. |
| 2004/0017387 A1 | 1/2004 | Soltero et al. |
| 2004/0024069 A1 | 2/2004 | Chen et al. |
| 2004/0057958 A1 | 3/2004 | Waggoner, Jr. et al. |
| 2004/0063606 A1 | 4/2004 | Chu et al. |
| 2004/0110285 A1 | 6/2004 | Lendlein et al. |
| 2004/0170685 A1 | 9/2004 | Carpenter et al. |
| 2004/0213759 A1 | 10/2004 | Zalipsky et al. |
| 2004/0213766 A1 | 10/2004 | Francois |
| 2004/0253293 A1 | 12/2004 | Shafiee et al. |
| 2004/0254151 A1 | 12/2004 | Ralston et al. |
| 2004/0258702 A1 | 12/2004 | Blonder et al. |
| 2005/0004378 A1 | 1/2005 | Mane et al. |
| 2005/0013812 A1 | 1/2005 | Dow et al. |
| 2005/0019366 A1 | 1/2005 | Zeldis |
| 2005/0019404 A1 | 1/2005 | Sung et al. |
| 2005/0025752 A1 | 2/2005 | Kutryk et al. |
| 2005/0043787 A1 | 2/2005 | Kutryk et al. |
| 2005/0053667 A1 | 3/2005 | Irvine et al. |
| 2005/0064602 A1 | 3/2005 | Kaufman et al. |
| 2005/0169968 A1 | 8/2005 | Elmaleh et al. |
| 2005/0175583 A1 | 8/2005 | Tamarkin et al. |
| 2005/0208091 A1 | 9/2005 | Pacetti |
| 2005/0216074 A1 | 9/2005 | Sahatjian et al. |
| 2005/0238689 A1 | 10/2005 | Carpenter et al. |
| 2005/0245637 A1 | 11/2005 | Hossainy et al. |
| 2005/0260259 A1 | 11/2005 | Bolotin |
| 2005/0265960 A1 | 12/2005 | Pacetti et al. |
| 2005/0271700 A1 | 12/2005 | DesNoyer et al. |
| 2005/0271701 A1 | 12/2005 | Cottone et al. |
| 2005/0287184 A1 | 12/2005 | Hossainy et al. |
| 2005/0288481 A1 | 12/2005 | DesNoyer et al. |
| 2006/0002947 A1 | 1/2006 | Humphreys et al. |
| 2006/0008532 A1 | 1/2006 | Govardhan et al. |
| 2006/0009498 A1 | 1/2006 | Whitcup |
| 2006/0013855 A1 | 1/2006 | Carpenter et al. |
| 2006/0024357 A1 | 2/2006 | Carpenter et al. |
| 2006/0036311 A1 | 2/2006 | Nakayama et al. |
| 2006/0074191 A1 | 4/2006 | DesNoyer et al. |
| 2006/0093842 A1 | 5/2006 | DesNoyer et al. |
| 2006/0115455 A1 | 6/2006 | Reed et al. |
| 2006/0121012 A1 | 6/2006 | Kutryk et al. |
| 2006/0135476 A1 | 6/2006 | Kutryk et al. |
| 2006/0159918 A1 | 7/2006 | Dugan et al. |
| 2006/0177416 A1 | 8/2006 | Turnell et al. |
| 2006/0188469 A1 | 8/2006 | Turnell et al. |
| 2006/0188486 A1 | 8/2006 | Carpenter et al. |
| 2006/0222546 A1 | 10/2006 | Lee et al. |
| 2006/0224331 A1 | 10/2006 | Watson Michnick et al. |
| 2006/0286064 A1 | 12/2006 | Turnell et al. |
| 2007/0042017 A1 | 2/2007 | Kutryk et al. |
| 2007/0055367 A1 | 3/2007 | Kutryk et al. |
| 2007/0066541 A1 | 3/2007 | Hughes et al. |
| 2007/0071790 A1 | 3/2007 | Ameer et al. |
| 2007/0077272 A1 | 4/2007 | Li et al. |
| 2007/0106035 A1 | 5/2007 | Gomurashvili et al. |
| 2007/0128250 A1 | 6/2007 | Katsarava et al. |
| 2007/0134332 A1 | 6/2007 | Turnell et al. |
| 2007/0141100 A1 | 6/2007 | Sung et al. |
| 2007/0141107 A1 | 6/2007 | Kutryk et al. |
| 2007/0156232 A1 | 7/2007 | Kutryk et al. |
| 2007/0160622 A1 | 7/2007 | Turnell et al. |
| 2007/0167605 A1 | 7/2007 | Chu et al. |
| 2007/0191932 A1 | 8/2007 | Kutryk et al. |
| 2007/0196422 A1 | 8/2007 | Kutryk et al. |
| 2007/0213801 A1 | 9/2007 | Kutryk et al. |
| 2007/0282011 A1 | 12/2007 | Gomurashvili et al. |
| 2007/0287987 A1 | 12/2007 | Katsarava et al. |
| 2007/0292476 A1 | 12/2007 | Landis et al. |
| 2007/0299155 A1 | 12/2007 | Carpenter et al. |
| 2008/0020015 A1 | 1/2008 | Carpenter et al. |
| 2008/0050419 A1 | 2/2008 | Katsarava et al. |
| 2008/0057024 A1* | 3/2008 | Zhang ............... A61K 9/0019 424/78.27 |
| 2008/0160089 A1 | 7/2008 | Vitiello et al. |
| 2008/0288057 A1 | 11/2008 | Carpenter et al. |
| 2008/0299174 A1 | 12/2008 | Gomurashvili et al. |
| 2009/0022772 A1 | 1/2009 | Carpenter et al. |
| 2009/0029937 A1 | 1/2009 | Chu et al. |
| 2009/0068743 A1 | 3/2009 | Turnell et al. |
| 2009/0202620 A1 | 8/2009 | Turnell et al. |
| 2009/0232874 A1 | 9/2009 | Chu et al. |
| 2009/0238854 A1 | 9/2009 | Pacetti et al. |
| 2009/0253809 A1 | 10/2009 | Gomurashvili et al. |
| 2010/0004390 A1 | 1/2010 | Turnell et al. |
| 2010/0040664 A1 | 2/2010 | Katsarava et al. |
| 2011/0027379 A1 | 2/2011 | Chu et al. |
| 2011/0137406 A1 | 6/2011 | Carpenter et al. |
| 2012/0027859 A1 | 2/2012 | Turnell et al. |
| 2012/0282299 A1 | 11/2012 | Delamarre et al. |
| 2012/0328706 A1 | 12/2012 | Turnell et al. |
| 2014/0105957 A1 | 4/2014 | Franken et al. |
| 2014/0120170 A1 | 5/2014 | Mihov et al. |
| 2014/0179802 A1 | 6/2014 | Franken et al. |
| 2014/0220099 A1 | 8/2014 | Draaisma et al. |
| 2015/0038415 A1 | 2/2015 | Zupancich |
| 2015/0216987 A1 | 8/2015 | Thies et al. |
| 2015/0240387 A1 | 8/2015 | Gillissen-Van Der Vight |
| 2015/0246001 A1 | 9/2015 | Zupancich et al. |
| 2015/0328374 A1 | 11/2015 | Mihov et al. |

FOREIGN PATENT DOCUMENTS

| | | |
|---|---|---|
| CA | 2225792 | 11/1997 |
| CA | 2419429 | 3/2002 |
| CN | 1281355 | 1/2001 |
| CN | 1296852 | 5/2001 |
| CN | 1837259 | 9/2006 |
| CN | 101168595 | 10/2006 |
| CN | 101168595 | 4/2008 |
| DE | 4224401 | 1/1994 |
| EP | 0147780 A3 | 3/1987 |
| EP | 0447719 B1 | 11/1993 |
| EP | 0396429 B1 | 7/1996 |
| EP | 0926184 | 6/1999 |
| EP | 0932399 B1 | 1/2006 |
| EP | 1313794 B1 | 11/2006 |
| EP | 1945682 | 7/2008 |
| JP | 11-240948 | 9/1999 |
| JP | 2004-507600 | 3/2004 |
| JP | 2005-139139 | 2/2005 |
| JP | 2005139139 | 6/2005 |
| JP | 2008027269 | 7/2008 |
| JP | 2008542393 | 11/2008 |
| JP | 2009-518289 | 5/2009 |
| JP | 2009-525342 | 12/2009 |
| JP | 2009-545516 | 12/2009 |
| WO | WO1994004642 | 3/1994 |
| WO | WO1997030104 | 8/1997 |
| WO | WO1998032398 | 7/1998 |
| WO | WO9929303 | 6/1999 |
| WO | WO99029302 | 6/1999 |

(56) References Cited

FOREIGN PATENT DOCUMENTS

| | | |
|---|---|---|
| WO | WO199058151 | 11/1999 |
| WO | WO1999061916 | 12/1999 |
| WO | WO2001028591 | 4/2001 |
| WO | WO2001051027 | 7/2001 |
| WO | WO2001091703 | 12/2001 |
| WO | 02/18477 | 3/2002 |
| WO | WO 02/18477 | 3/2002 |
| WO | WO2002018477 A2 | 3/2002 |
| WO | WO03024420 | 3/2003 |
| WO | WO2003062298 | 7/2003 |
| WO | WO2004039944 | 5/2004 |
| WO | WO2004040339 | 5/2004 |
| WO | WO2005027906 | 3/2005 |
| WO | WO2005061024 | 7/2005 |
| WO | WO2005097186 | 10/2005 |
| WO | WO2005112587 | 12/2005 |
| WO | WO2005112884 | 12/2005 |
| WO | WO2005118681 | 12/2005 |
| WO | WO2006050091 | 5/2006 |
| WO | WO2006083874 | 8/2006 |
| WO | WO2006088647 | 8/2006 |
| WO | WO2006108167 | 10/2006 |
| WO | WO2006132950 | 12/2006 |
| WO | WO2007035938 A2 | 3/2007 |
| WO | WO2007050415 | 5/2007 |
| WO | WO2007067744 | 6/2007 |
| WO | 2007/089931 | 8/2007 |
| WO | WO2007089870 | 8/2007 |
| WO | WO2007089931 | 8/2007 |
| WO | WO2007130477 | 11/2007 |
| WO | WO2007133616 | 11/2007 |
| WO | 2008/048298 | 4/2008 |
| WO | WO2008048298 | 4/2008 |
| WO | WO2008157254 | 12/2008 |
| WO | WO2009012449 A1 | 1/2009 |
| WO | WO2009015143 | 1/2009 |
| WO | WO2009026543 | 2/2009 |
| WO | WO20100045241 | 4/2010 |
| WO | WO 2011/045443 | 4/2011 |
| WO | WO2011045443 A1 | 4/2011 |
| WO | WO 2011045443 A1 * | 4/2011 ............. A61L 27/34 |
| WO | WO2011146483 | 11/2011 |
| WO | WO2012175746 | 12/2012 |
| WO | WO2012175748 | 12/2012 |
| WO | WO2007038246 | 4/2017 |

OTHER PUBLICATIONS

International Search Report for PCT/EP2012/062267, dated Aug. 30, 2012.
Chinese Office Action and Search Report, Appln No. 201280031014.9 dated Jan. 6, 2015.
Notice of Reasons for Rejection, JP Appln. No. P2014-516391 (Jun. 7, 2016).
Gautier et al, Alkylated poly(L-lysine citramide) as models to investigate the ability of amphiphillic macromolecular drug carriers to physically entrap lipophilic compounds in aqueous media, Journal of Controlled Release 60 (1999( 235-247.
Eccleston et al, pH-responsive pseudo-peptides for cell membrane disruption, Journal of Controlled Release 69 (2000) 297-307.
Eccleston et al, Synthetic routes to responsive polymers; co-polycondensation of tri-functional amino acids with diacylchlorides, Reactive & Functional Polymers 42 (1999) 147-161.
Asin, et al., Sequential Poly(ester amide)s based on Glycine, Diols, and Dicarboxylic Acids: Thermal Polyesterification verus Interfacial Polyamidation. Characterization of Polymers Containing Stiff Units, J. Polym. Sci. Part A: Polm Chem, 2001, 4283-4293, 39(4).
Becker, et al., Prevention of Postoperative Abdominal Adhesions by a Sodium Hyaluronate-Based Bioresorbable Membrane: A Prospective, Randomized, Double-Multicenter Study, J. Am. Coil. Surg, 1996, pp. 297-306, 183.
Eccleston et al, pH-responsive pseudo-peptides for cell membrane disruption, Journal of Controlled Release, 2000, pp. 297-307, vol. 69, No. 2.
Eccleston et al., Synthetic routes to responsive polymers, Reactive & Functional Polymers, 1999, pp. 147-161, vol. 42, No. 2.
Furchgott and Zawadzki, The obligatory role of endothelial cells in the relaxation of arterial smooth muscle by acetylcholine, Inature, 1980, pp. 373-376, 388.
Gautier et al, Alkylated poly(L-lysine citramide) as models to investigate the ability, Journal of Controlled release, 1999, pp. 235-247, vol. 60, No. 2-3.
Gomurashvili , et al, Amino Acid Based Bioanalogous Polymers. Synthesis and Study of New Poly(Ester Amide)S Composed of Hydrophobic α-Amino Acids and Dianhydrohexitoles, J.M.S.—Pure Appl. Chem, 2000, pp. 215-227, A37(3).
Gomurashvili, et al., From Drug-Eluting Stents to Biopharmaceuticals: Poly(ester amide) a Versatile New Bioabsorable Biopolymer. In: Polymers for Biomedical Applications, ACS Symposium Series; American Chemical Society, 2008, pp. 10-26, Chapter 2.
Guo, et al., Synthesis and Characterization of Novel Biodegradable Unsaturated Poly(ester amide)/Poly(ethylene glycol) Diacrylate Hydrogels, Journal of Polymer Science: Part A: Polymer Chemistry, 2005, pp. 3932-3944, 43.
Huang, et al., Biodegradable Polymers: Chymotrypsin Degradationi of a Low Molecular Weight Poly(ester-Urea) Containing Phenylalanine, J. Appl. Polym. Sci, 1979, pp. 429-437, 23.
Kartvelishvili, et al., Ämino acid based bioanalogous polymers. Novel regular poly(ester urethane)s and poly(ester urea)s based on bis(L-phenylalanine) α, CO-alkylene diesters, Macromol. Chem. Phys, 1997, pp. 1921-1932, 198.
Qian, et al., Preparation of biodegradable polyesteramide microspheres, Colloid Polym. Sci, 2004, pp. 1083-1088, 282.
Saotome et al, Novel Enzymatically Degradable Polymers Comprising a-Amino Acid, 1,2-Ethanediol, and Adipic Acid, Chemistry Letters, 1991, pp. 21-24, No Volume.
Tsitlanadze et al., Biodegradation of amino-acid-based poly(ester amide)s: in vitro weight loss and preliminary in vivo studies, Journal of Biomaterials Science, Jan. 1, 2004, 24 Pages, vol. 15.
Yokoe et al, Biodegradable Polymers Based on Renewable Resources. VII. Novel Random and Alternating Copolycarbonates from 1,4:3,6-Dianhydrohexitols and Aliphatic Diols, Journal of Polymer Science: Part A: Polymer Chemistry, 2003, pp. 2312-2331, 41.
Final Office Action in U.S. Appl. No. 14/432,349 dated Apr. 12, 2017.
U.S. Appl. No. 14/432,349 Non Final Office Action dated Aug. 23, 2017.

\* cited by examiner

PARTICLES COMPRISING POLYESTERAMIDE COPOLYMERS FOR DRUG DELIVERY

This application is the U.S. national phase of International Application No. PCT/EP2012/062267 filed 25 Jun. 2012 which designated the U.S. and claims priority to EP Patent Application No. 11171191.7 filed 23 Jun. 2011, the entire contents of each of which are hereby incorporated by reference.

The present invention relates to particles comprising polyesteramide co-polymers. The present invention also relates to the particles for use in medical applications especially for use in the delivery of bioactive agents.

Biodegradable polyesteramides are known in the art, in particular α-amino acid-diol-diester based polyesteramides (PEA) are known from G. Tsitlanadze, et al. J. Biomater. Sci. Polym. Edn. (2004) 15:1-24. These polyesteramides provide a variety of physical and mechanical properties as well as biodegradable profiles which can be adjusted by varying three components in the building blocks during their synthesis: naturally occurring amino acids and, therefore, hydrophobic alpha-amino acids, non-toxic fatty diols and aliphatic dicarboxylic acids.

WO2002/18477 specifically refers to alpha-amino acid-diol-diester based polyesteramides (PEA) copolymers of formula I, further referred to as PEA-I,

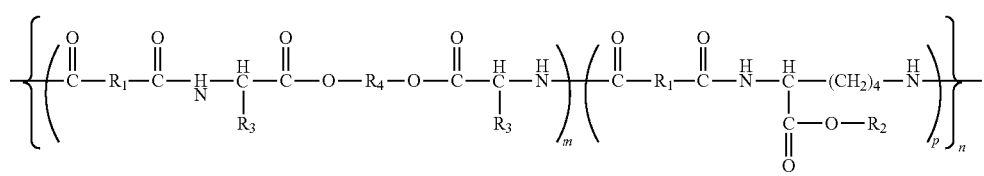

Formula I wherein:
m varies from 0.1 to 0.9; p varies from 0.9 to 0.1; n varies from 50 to about 150;
each R1 is independently $(C_1\text{-}C_{20})$alkylene;
each $R_2$ is independently hydrogen or $(C_6\text{-}C_{10})$aryl$(C_1\text{-}C_6)$alkyl;
each $R_3$ is independently hydrogen, $(C_1\text{-}C_6)$ alkyl, $(C_2\text{-}C_6)$alkenyl, $(C_2\text{-}C_6)$alkynyl, or $(C_6\text{-}C_{10})$aryl$(C_1\text{-}C_6)$ alkyl; and
each $R_4$ is independently $(C_2\text{-}C_{20})$alkylene.

PEA-I is a random copolymer comprising m units build upon alpha-amino acids, diols and an aliphatic dicarboxylic acids, which are copolymerized with p units build upon an aliphatic dicarboxylic acid and L-lysine.

WO2008/0299174 discloses particles based on random PEA co-polymers according to Formula II comprising at least two linear saturated or unsaturated aliphatic diol residues into two bis-(α amino acid)-based diol-diesters.

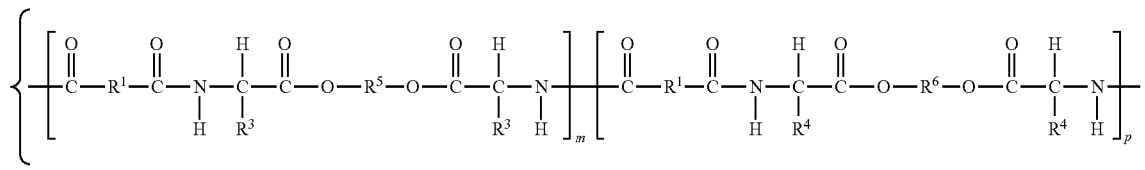

Formula II

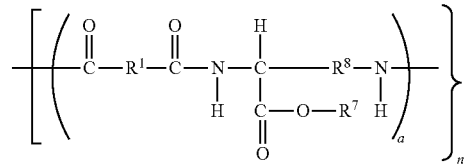

wherein
   m is 0.01 to 0.99; p is 0.99 to 0.01; and q is 0.99 to 0.01; and wherein n is 5 to 100; wherein $R_1$ can be independently selected from the group consisting of $(C_2-C_{20})$alkylene, $(C_2-C_{20})$alkenylene, —($R_9$—CO—O—$R_{10}$—O—CO—$R_9$)—, —$CHR_{11}$—O—CO—$R_{12}$—COOC$R_{11}$— and combinations thereof;

$R_3$ and $R_4$ in a single co-monomer m or p, respectively, can be independently selected from the group consisting of hydrogen, $(C_1-C_6)$alkyl, $(C_2-C_6)$alkenyl, $(C_2-C_6)$alkynyl, $(C_6-C_{10})$aryl, $(C_1-C_6)$alkyl, —$(CH_2)$SH, —$(CH_2)_2$S$(CH_3)$, —$CH_2$OH, —CH(OH)$CH_3$, —$(CH_2)_4$NH$_3$+, —$(CH_2)_3$NHC(=NH$_2$+)NH$_2$, —$CH_2$COOH, —$(CH_2)$COOH, —$CH_2$—CO—NH$_2$, —$CH_2CH_2$—CO—NH$_2$, —$CH_2CH_2$COOH, $CH_3$—$CH_2$—CH$(CH_3)$—, $(CH_3)_2$—CH—$CH_2$—, $H_2$N—$(CH_2)_4$—, Ph—$CH_2$—, CH=C—$CH_2$—, HO-p-Ph-$CH_2$—, $(CH_3)_2$—CH—, Ph-NH—, NH—$(CH_2)_3$—C—, NH—CH=N—CH=C—$CH_2$—.

$R_5$ is can be selected from the group consisting of $(C_2-C_{20})$alkylene, $(C_2-C_{20})$alkenylene, alkyloxy or oligoethyleneglycol;

$R_6$ can be selected from bicyclic-fragments of 1,4:3,6-dianhydrohexitols of structural formula (III);

Formula III

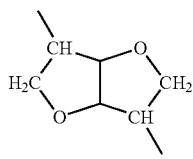

$R_7$ can be hydrogen, $(C_6-C_{10})$ aryl, $(C_1-C_6)$ alkyl or a protecting group such as benzyl- or a bioactive agent;
   $R_8$ can be independently $(C_1-C_{20})$ alkyl or $(C_2-C_{20})$alkenyl;
   $R_9$ or $R_{10}$ can be independently selected from $C_2-C_{12}$ alkylene or $C_2-C_{12}$ alkenylene.
   $R_{11}$ or $R_{12}$ can be independently selected from H, methyl, $C_2-C_{12}$ alkylene or $C_2-C_{12}$ alkenylene.

If in the random polyesteramide co-polymer of Formula (II) m+p+q=1, q=0.25, p=0.45 whereby $R_1$ is —$(CH_2)_8$; $R_3$ and $R_4$ in the backbone units m and p is leucine, —$R_5$ is hexane, and $R_6$ is a bicyclic-fragments of 1,4:3,6-dianhydrohexitols of structural formula (III); $R_7$ is benzyl group and $R_8$ is —$(CH2)4$- this polyesteramide is further referred to as PEA-III-Bz. In case that $R_7$ is H, the polyesteramide is further referred to as PEA-III-H.

In case that m+p+q=1, q=0.25, p=0.75 and m=0, whereby $R_1$ is —$(CH_2)_4$; $R_3$ is $(CH_3)_2$—CH—$CH_2$—, $R_7$ is benzyl, $R_8$ is —$(CH_2)_4$; and $R_6$ is selected from bicyclic-fragments of 1,4:3,6-dianhydrohexitols of structural formula (II), the polyesteramide is further referred to as PEA-IV-Bz, in case that $R_7$ is H the polyesteramide is further referred to as PEA-IV-H.

WO2008/0299174 further discloses that the polyesteramides and particles made thereof, facilitate the in vivo release of bioactive agents dispersed in the polymer at a controlled release rate, which is specific and constant over a prolonged period. It is furthermore disclosed that the PEA break down in vivo via enzymes to produce biological α-amino acids upon break down products which are substantially non-inflammatory.

However in some medical areas there is a need for polymers and drug delivery forms such as particles comprising polymers which degrade hydrolytically instead of enzymatically. This need exists for example in ophthalmology where the delivery of drugs intraocularly is a particular problem. The eye is divided into two chambers; the anterior segment which is the front of the eye, and the posterior segment which is the back of the eye. In the back of the eye, in the vitreous, less or no enzymes are present such that for example particles based on enzymatically degradable polyesteramides will not degrade or will degrade too slow. If the particles degrade too slowly, the release of the bioactive agents will also be influenced negatively.

Beside the issue of enzymatic degradation it has further been observed that particles, such as micro- and nanoparticles comprising the above mentioned polyesteramides such as PEA-III-Bz tend to aggregate when exposed to aqueous medium. These properties could have a negative effect on re-dispersibility and injectability of the particles and respectively on the administration of such particles for drug delivery purposes. Furthermore, the aggregation and agglomeration of the particles would result in a change of the effective surface area of the particles directly impacting the drug release rate in an unpredictable and hardly reproducible way.

There is thus still a need in the art for new and better particle delivery system comprising biodegradable polyesteramides which provide for continuous delivery of bioactive agents over a sustained period of time and which moreover takes away the above mentioned disadvantages of particle aggregation.

The object of the present invention is therefore to provide micro- and nanoparticles comprising biodegradable polyesteramide copolymers which take away the above mentioned disadvantages.

The object of the present invention is achieved by providing micro- and nanoparticles comprising a biodegradable poly(esteramide) copolymer (PEA) according to structural formula (IV), Formula IV

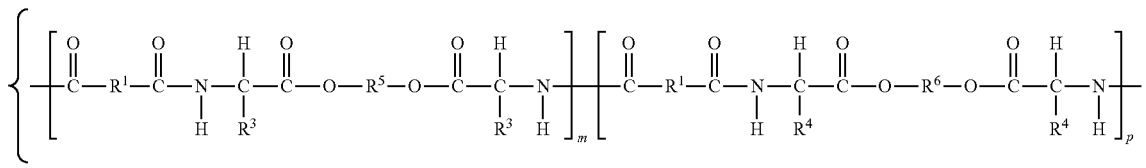

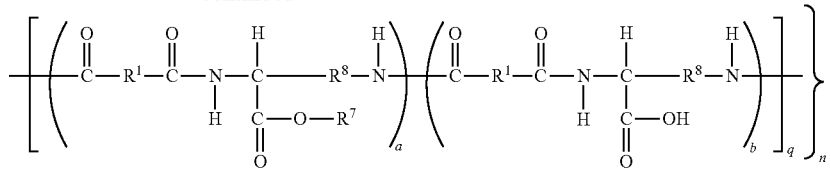

wherein
m+p varies from 0.9-0.1 and q varies from 0.1 to 0.9
m+p+q=1 whereby m or p could be 0
n is about 5 to about 300;

$R_1$ is independently selected from the group consisting of $(C_2-C_{20})$ alkylene, $(C_2-C_{20})$ alkenylene, —$(R_9$—CO—O—$R_{10}$—O—CO—$R_9)$—, —CHR$_{11}$—O—CO—$R_{12}$—COOCR$_{11}$— and combinations thereof;

$R_3$ and $R_4$ in a single backbone unit m or p, respectively, are independently selected from the group consisting of hydrogen, $(C_1-C_6)$alkyl, $(C_2-C_6)$alkenyl, $(C_2-C_6)$alkynyl, $(C_6-C_{10})$aryl, $(C_1-C_6)$alkyl, —$(CH_2)$SH, —$(CH_2)_2S(CH_3)$, —$CH_2OH$, —CH(OH)CH$_3$, —$(CH_2)_4NH_3+$, —$(CH_2)_3NHC(=NH_2+)NH_2$, —CH$_2$COOH, —$(CH_2)$COOH, —CH$_2$—CO—NH$_2$, —CH$_2$CH$_2$—CO—NH$_2$, —CH$_2$CH$_2$COOH, CH$_3$—CH$_2$—CH(CH$_3$)—, $(CH_3)_2$—CH—CH$_2$—, H$_2$N—$(CH_2)_4$—, Ph-CH$_2$—, CH=C—CH$_2$—, HO-p-Ph-CH$_2$—, $(CH_3)_2$—CH—, Ph-NH—, NH—$(CH_2)_3$—C—, NH—CH=N—CH=C—CH$_2$—;

$R_5$ is selected from the group consisting of $(C_2-C_{20})$ alkylene, $(C_2-C_{20})$alkenylene, alkyloxy or oligoethyleneglycol $R_6$ is selected from bicyclic-fragments of 1,4:3,6-dianhydrohexitols of structural formula (III);

Formula III

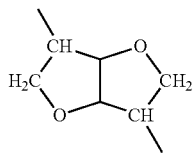

$R_7$ is selected from the group consisting of $(C_6-C_{10})$ aryl $(C_1-C_6)$ alkyl $R_8$ is —$(CH_2)_4$—;

$R_9$ or $R_{10}$ are independently selected from $C_2-C_{12}$ alkylene or $C_2-C_{12}$ alkenylene.

$R_{11}$ or $R_{12}$ are independently selected from H, methyl, $C_2-C_{12}$ alkylene or $C_2-C_{12}$ alkenylene whereby a is at least 0.05, b is at least 0.05 and a+b=1.

Surprisingly it has been found that micro- or nanoparticles comprising the biodegradable polyesteramides of formula IV in which both L-Lysine-H as well L-lysine-benzyl are present, (hereinafter referred to as PEA-H/Bz) provide unexpected properties in terms of release, degradation and aggregation properties. It has been found that micro- or nanoparticles comprising PEA-H/Bz co-polymers provide a sustained release of bioactive agents and degrade hydrolytically at physiological conditions via bulk erosion mechanism in contrast with the PEA polymers known in the prior art that degrade only in presence of certain classes of enzymes by surface erosion.

It is even more unexpected that micro- or nanoparticles of the biodegradable polyesteramides of Formula IV do not aggregate in aqueous environment even exposed at temperature above their wet Tg for a long time. The ('wet') glass transition temperature ($T_g$) is the glass transition temperature when the polymesteramide is exposed to an aqueous environment.

For example PEA-III-Bz of formula II where m+p+q=1, q=0.25, p=0.45 and m=0.3, whereby $R_1$ is —$(CH_2)_8$; $R_4$ and $R_3$ are $(CH_3)_2$—CH—CH$_2$—, $R_7$ is benzyl, $R_8$ is —$(CH_2)_4$; and $R_6$ is selected from bicyclic-fragments of 1,4:3,6-dianhydrohexitols of structural formula (III), is a polymer with "a wet glass transition temperature" of about 24° C. as determined after exposure to 0.1 M PBS buffer at 37° C. Particles of this polymer were prepared via standard water/oil/water (w/o/w) emulsion technique, dispersed in 0.1 M PBS buffer and kept at 37° C. Already in 24 hours the particles started to form aggregates, they fused together at later stage and became an unshaped mass. These properties are also representative for the prior art polyesteramide as described in for example in WO2008/0299174.

Alternatively, when analogous micro- or nanoparticles were prepared from random co-polymers of PEA-III-H/Bz 50% H of formula IV wherein m+p+q=1, q=0.25, p=0.45 and m=0.3, a is 0.5, a+b=1 and whereby $R_1$ is —$(CH_2)_8$; $R_4$ and $R_3$ are —$(CH_3)_2$—CH—CH$_2$—, $R_7$ is benzyl, $R_8$ is —(CH2)4; and $R_6$ is selected from bicyclic-fragments of 1,4:3,6-dianhydrohexitols of structural formula (III) with "a wet" glass transition temperature of 21° C., the obtained particles did not aggregate in the solution during the entire experimental time of 21 days.

Figure 5:
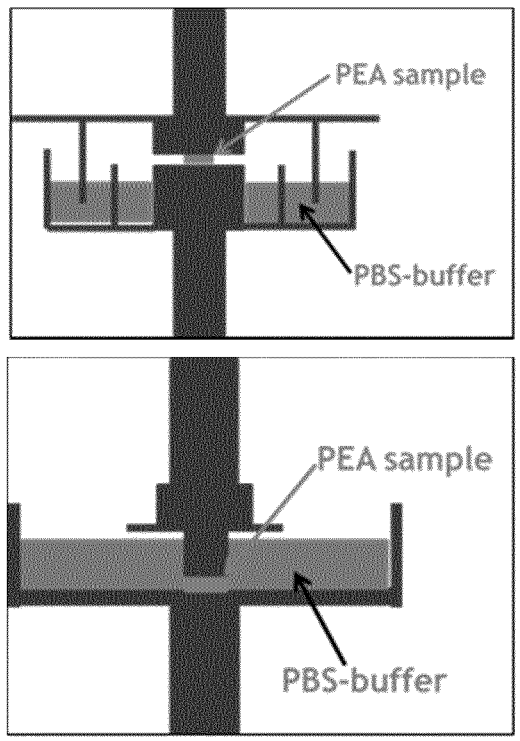

The above mentioned 'wet' $T_g$'s were determined by performing temperature ramp tests from 45 to 0° C. (cooling @5° C./min) at an angular frequency of 1 Hz (6.28 rad/s) and a variable strain (autostrain control enabled) with an initial value of 0.1%. The gap was controlled manually to ensure a constant axial force (compression) on the sample ($F_N$~30 grams). This constant compressive force is necessary to prevent a loss of contact between the sample and the parallel plates. FIG. 5 gives a schematic representation of the geometry as it was used for 'wet' Tg measurement.

Also the degradation properties of the micro- or nanoparticles comprising the PEA-H/Bz co-polymers according to the present invention are markedly different than the degradation properties of prior art polymers such as PEA-I, PEA-III, PEA-IV or PLGA. It has been found that the micro- or nanoparticles comprising the PEA-H/Bz co-polymers seem to degrade hydrolytically and mainly via surface erosion mechanism whereas the known PEA particles degrade mainly via an enzymatic degradation process and via a bulk erosion mechanism. Also other prior art polymers such as PLGA or PLLA seem to degrade mainly via bulk erosion mechanism. This is confirmed in FIG. 1.

A further disadvantage in the degradation of for example PLGA and PLLA particles is the fact that they often result in a pH drop which is undesired because it may influence the stability of the bioactive agent to be released from the micro- or nanoparticles. After four weeks of degradation PLGA particles start to release highly acidic degradation products resulting in pH drop. In contrast the pH of the PEA-I-H/Bz micro- or nanoparticles did not change along the entire 13 weeks. It seems that lysine free carboxylic groups and acidic species generated during the degradation are in a right balance to catalyze bonds cleavage along the polyesteramide chain but not compromising the optimal physiological conditions. From experiments it has surprisingly been found that micro- or nanoparticles of PEA-H/Bz do not show a significant pH drop.

The above findings confirm that micro- or nanoparticles comprising the polyesteramides of formula IV in which both L-Lysine-H as well L-lysine-benzyl are present in a certain ratio provides surprising properties addressing better the needs of micro- and nanoparticles in drug delivery.

In the following embodiments of the present invention n in Formula IV preferably varies from 50-200 and a may be at least 0.15, more preferably at least 0.5, most preferably 0.75, even more preferably at least 0.8.

In one embodiment the micro- or nanoparticles comprising the biodegradable polyesteramide copolymer according to Formula (IV) comprise p=0 and m+q=1 whereby m=0.75, a=0.5 and a+b=1, $R_1$ is $(CH_2)_8$, $R_3$ is —$(CH_3)_2$—CH—$CH_2$—, $R_5$ is hexyl, $R_7$ is benzyl and $R_8$ is —$(CH_2)_4$—. This polyesteramide is referred to as PEA-I-H/Bz 50% H.

In another preferred embodiment of the present invention the micro- or nanoparticles comprising the biodegradable polyesteramide copolymer according to Formula (IV) comprise m+p+q=1, q=0.25, p=0.45 and m=0.3 whereby a is 0.5 and a+b=1 and whereby $R_1$ is —$(CH_2)_8$; $R_3$ and $R_4$ respectively are —$(CH_3)_2$—CH—$CH_2$—, $R_5$ is selected from the group consisting of $(C_2-C_{20})$alkylene, $R_6$ is selected from bicyclic-fragments of 1,4:3,6-dianhydrohexitols of structural formula (III); $R_7$ is benzyl and $R_8$ is —$(CH_2)_4$. This polyesteramide is referred to as PEA-III-H/Bz 50% H.

In a still further preferred embodiment of the present invention micro- or nanoparticles comprising the biodegradable polyesteramide copolymer according to Formula (IV) comprise m+p+q=1, q=0.25, p=0.45 and m=0.3 whereby a is 0.75 and a+b=1, $R_1$ is —$(CH_2)_8$; $R_4$ is $(CH_3)_2$—CH—$CH_2$—, $R_7$ is benzyl, $R_8$ is —$(CH_2)_4$— and $R_6$ is selected from bicyclic fragments of 1,4:3,6-dianhydrohexitols of structural formula (III). This polyesteramide is referred to as PEA-III-H/Bz 25% H.

In a yet further preferred embodiment of the present invention the micro- or nanoparticles comprising the biodegradable poly(esteramide) copolymer according to Formula (IV) comprise m+p+q=1, q=0.1, p=0.30 and m=0.6 whereby a=0.5 and a+b=1. $R_1$ is —$(CH_2)_4$; $R_3$ and $R_4$ respectively, are $(CH_3)_2$—CH—$CH_2$—; $R_5$ is selected from the group consisting of $(C_2-C_{20})$alkylene, $R_7$ is benzyl, $R_8$ is —$(CH_2)_4$— and $R_6$ is selected from bicyclic-fragments of 1,4:3,6-dianhydrohexitols of structural formula (III). This polyesteramide is referred to as PEA-II-H/Bz50% H.

As used herein, the term "alkyl" refers to a straight or branched chain hydrocarbon group including methyl, ethyl, n-propyl, isopropyl, n-butyl, isobutyl, tert-butyl, n-hexyl, and the like.

As used herein, the term "alkylene" refers to a divalent branched or unbranched hydrocarbon chain containing at least one unsaturated bond in the main chain or in a side chain.

As used herein, the term "alkenyl" refers to a straight or branched chain hydrocarbon group containing at least one unsaturated bond in the main chain or in a side chain.

As used herein, "alkenylene", refers to structural formulas herein to mean a divalent branched or unbranched hydrocarbon chain containing at least one unsaturated bond in the main chain or in a side chain.

As used herein, "alkynyl", refers to straight or branched chain hydrocarbon groups having at least one carbon-carbon triple bond.

The term "aryl" is used with reference to structural formulas herein to denote a phenyl radical or an ortho-fused bicyclic carbocyclic radical having about nine to ten ring atoms in which at least one ring is aromatic. Examples of aryl include, but are not limited to, phenyl, naphthyl, and nitrophenyl.

The term biodegradable" refers to material which is capable of being completely or substantially degraded or eroded when exposed to an in vivo environment or a representative in vitro. A polymer is capable of being degraded or eroded when it can be gradually broken-down, resorbed, absorbed and/or eliminated by, for example, hydrolysis, enzymolysis, oxidation, metabolic processes, bulk or surface erosion, and the like within a subject. The terms "bioabsorbable" and "biodegradable" are used interchangeably in this application.

The term "random copolymer" as used herein refers to the distribution of the m, p and q units of the polyesteramide of formula (IV) in a random distribution.

As used herein, particles include micro- or nano-particles.

At least one of the alpha-amino acids used in the polyesteramide co-polymers according to formula (IV) is a natural alpha-amino acid. For example, when the $R_3$s or $R_4$s are benzyl the natural alpha-amino acid used in synthesis is L-phenylalanine. In alternatives wherein the $R_3$s or $R_4$s are —$CH_2$—$CH(CH_3)_2$, the co-polymer contains the natural amino acid, leucine. By independently varying the $R_3$s and $R_4$s within variations of the two co-monomers as described herein, other natural alpha-amino acids can also be used, e.g., glycine (when the $R_3$ or $R_4$ are H), alanine (when the $R_3$ or $R_4$ are $CH_3$), valine (when the $R_3$ or $R_4$ are —$CH(CH_3)_2$, isoleucine (when the $R_3$ or $R_4$ are —$CH(CH_3)$—$CH_2$—$CH_3$), phenylalanine (when the $R_3$ or $R_4$ are $CH_2$—$C_6H_5$), lysine (when the $R_3$ or $R_4$ $(CH_2)_4$—$NH_2$); or methionine (when the $R_3$s or $R_4$s are —$(CH_2)_2S(CH_3)$, and mixtures thereof.

The polyesteramide co-polymers of Formula (IV) preferably have an average number molecular weight (Mn) ranging from 15,000 to 200,000 Daltons. The polyesteramide co-polymers described herein can be fabricated in a variety of molecular weights and a variety of relative proportions of the m, p, and q units in the backbone. The appropriate molecular weight for a particular use is readily determined by one skilled in the art. A suitable Mn will be in the order of about 15,000 to about 100,000 Daltons, for example from about 30,000 to about 80,000 or from about 35,000 to about 75,000. Mn is measured via GPC in THF with polystyrene as standard.

The basic polymerization process of polyesteramides is based on the process described by G. Tsitlanadze, et al. J. Biomater. Sci. Polym. Edn. (2004) 15:1-24, however different building blocks and activating groups were used.

The polyesteramides of Formula (IV) are for example synthesized as shown in scheme 1; via solution polycondensation of para-toluene sulfonate di-amines salts (X1, X2, X3) with activated di-acids (Y1). Typically dimethylsulfoxide or dimethylformamide are used as solvent. Typically as a base triethylamide is added, the reaction is carried out under an inert atmosphere at 60° C. for 24-72 hours under constant stirring. Subsequently the obtained reaction mixture is purified via a water precipitation followed by an organic precipitation and filtration. Drying under reduced pressure yields the polyesteramide.

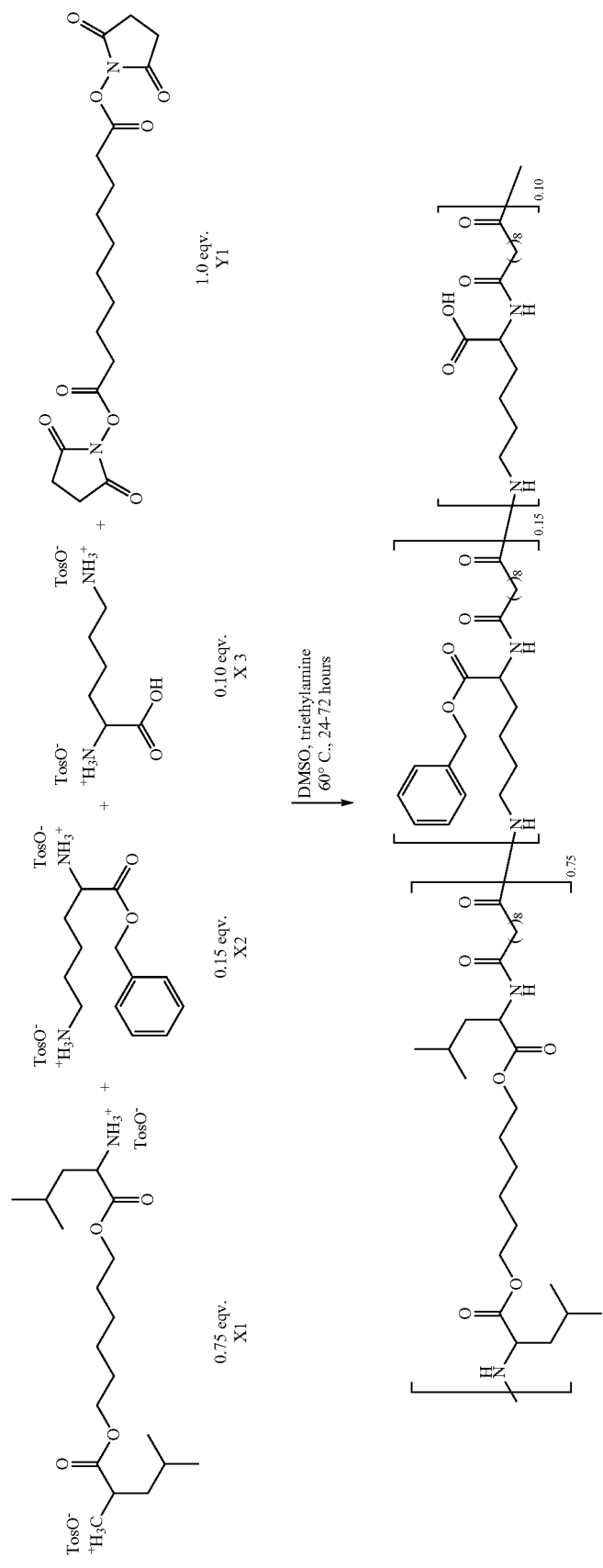
Scheme 1: schematic representation of PEA polymerization process, including some typical monomers.

Typically, the average diameter of the microparticles given by the Fraunhofer theory in volume percent ranges from 10 nm to 1000 μm. The preferred average diameter depends on the intended use. For instance, in case the microparticles are intended for use as an injectable drug delivery system, in particular as an intravascular drug delivery system, an average diameter of 1-40 μm may be desired, more preferably an average diameter of 20-40 μm may be desired.

It is envisaged that particles with an average diameter of less than 1000 nm are nanoparticles. Typically nanoparticles with a size of less than 800 nm, in particular less than 500 nm are useful for intracellular purposes. For such purposes, the average diameter preferably ranges from 50-500 nm, more preferably it ranges from 100-300 nm.

In other applications, larger dimensions may be desirable, for instance an average diameter in the range of 1-100 μm or even 1-1000 μm. Preferably the average diameter of the microparticles ranges from 10-100 μm. More preferably the average diameter of the microparticles range from 20-60 μm. Even more preferably the average diameter of the microparticles range from 20-40 μm. In particular, the particle diameter as used herein is the diameter as determinable by a Malven Mastersizer 2000. Particles can be defined and classified in various different ways depending on their specific structure, size, or composition, see e.g. Encyclopaedia of Controlled drug delivery Vol2 M-Z Index, Chapter: Microencapsulation Wiley Interscience, page 493-496.

If particles are too small or non-analyzable by light scattering which may be the case with nanoparticles because of their optical properties, then scanning electron microscopy (SEM) or transmission electron microscopy (TEM) can be used.

The micro- and nanoparticles of the present invention may be used as a delivery system for bioactive agents but also for the delivery of diagnostic aids or imaging agents.

The micro- or nanoparticles according to the present invention may comprise one or more bioactive agents. The bioactive agent(s) may be more or less homogeneously dispersed within the micro- or nanoparticles. The bioactive agent may also be located within the micro- or nanoparticle core or shell.

In particular, the bioactive agent may be selected from the group of nutrients, pharmaceuticals, small molecule drugs, proteins and peptides, vaccines, genetic materials, (such as polynucleotides, oligonucleotides, plasmids, DNA and RNA), diagnostic agents, and imaging agents. The bioactive agent, such as an bioactive pharmacologic ingredient (API), may demonstrate any kind of activity, depending on the intended use.

The bioactive agent may be capable of stimulating or suppressing a biological response. The bioactive agent may for example be chosen from growth factors (VEGF, FGF, MCP-1, PIGF, antibiotics (for instance penicillin's such as B-lactams, chloramphenicol), anti-inflammatory compounds, antithrombogenic compounds, anti-claudication drugs, anti-arrhythmic drugs, anti-atherosclerotic drugs, antihistamines, cancer drugs, vascular drugs, ophthalmic drugs, amino acids, vitamins, hormones, neurotransmitters, neurohormones, enzymes, signalling molecules and psychoactive medicaments.

The bioactive agents can have antiproliferative or anti-inflammatory properties or can have other properties such as antineoplastic, antiplatelet, anti-coagulant, anti-fibrin, anti-thrombotic, antimitotic, antibiotic, antiallergic, or antioxidant properties. Examples of antiproliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-0-(3-hydroxy)propyl-rapamycin, 40-O-[2-(2-hydroxy)ethoxy]ethyl-rapamycin, and 40-0-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia AND Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein Hb/nia platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck AND Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-I-oxyl (4-amino-TEMPO), estradiol, anticancer agents, dietary supplements such as various vitamins, and a combination thereof. Examples of anti-inflammatory agents including steroidal and nonsteroidal anti-inflammatory agents include biolimus, tacrolimus, dexamethasone, clobetasol, corticosteroids or combinations thereof. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck AND Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells.

Further examples of specific bioactive agents are neurological drugs (amphetamine, methylphenidate), alpha1 adrenoceptor antagonist (prazosin, terazosin, doxazosin, ketenserin, urapidil), alpha2 blockers (arginine, nitroglycerin), hypotensive (clonidine, methyldopa, moxonidine, hydralazine minoxidil), bradykinin, angiotensin receptor blockers (benazepril, captopril, cilazepril, enalapril, fosinopril, lisinopril, perindopril, quinapril, ramipril, trandolapril, zofenopril), angiotensin-1 blockers (candesartan, eprosartan, irbesartan, losartan, telmisartan, valsartan), endopeptidase (omapatrilate), beta2 agonists (acebutolol, atenolol, bisoprolol, celiprolol, esmodol, metoprolol, nebivolol, betaxolol), beta2 blockers (carvedilol, labetalol, oxprenolol, pindolol, propanolol) diuretic actives (chlortalidon, chlorothiazide, epitizide, hydrochlorthiazide, indapamide, amiloride, triamterene), calcium channel blockers (amlodipin, barnidipin, diltiazem, felodipin, isradipin, lacidipin, lercanidipin, nicardipin, nifedipin, nimodipin, nitrendipin, verapamil), anti arthymic active (amiodarone, solatol, diclofenac, flecamide) or ciprofloxacin, latanoprost, flucloxacillin, rapamycin and analogues and limus derivatives, paclitaxel, taxol, cyclosporine, heparin, corticosteroids (triamcinolone acetonide, dexamethasone, fluocinolone acetonide), anti-angiogenic (iRNA, VEGF antagonists: bevacizumab, ranibizumab, pegaptanib), growth factor, zinc finger transcription factor, triclosan, insulin, salbutamol, oestrogen, norcantharidin, microlidil analogues, prostaglandins, statins, chondroitinase, diketopiperazines, macrocycli compounds, neuregulins, osteopontin, alkaloids, immuno suppressants, antibodies, avidin, biotin, clonazepam. The foregoing substances can also be used in the form of prodrugs or co-drugs thereof. The foregoing substances also include metabolites thereof and/or prodrugs of the metabolites. The foregoing substances are listed by way of example and are not meant to be limiting.

In accordance with the present invention, if a bioactive agent is present, the concentration of one or more bioactive agent(s) in the micro- or nanoparticles, is preferably at least 1 wt %, based on the total weight of the micro- or nanoparticles, in particular at least 5 wt. %, more in particular at least 10 wt %. The concentration may be up to 90 wt %, up to 70 wt. %, up to 50 wt. % or up to 30 wt. %, as desired.

It is also possible to functionalise at least the surface of the microparticles since the polymer naturally contains free carboxyl groups along the polymer chain, in particular with a signalling molecule, an enzyme or a receptor molecule, such as an antibody. The receptor molecule may for instance be a receptor molecule for a component of interest, which is to be purified or detected, e.g. as part of a diagnostic test, making use of the particles of the present invention. Suitable functionalisation methods may be based on a method known in the art. In particular, the receptor molecule may be bound to the biodegradable polyesteramide of which the particles are prepared via an available or post introduced reactive group Since the micro- or nanoparticles comprise —COOH groups, it is possible to functionalize these —COOH groups with carbodiimide which may further react with a hydroxyl group or amino group of a target functional moiety to be coupled to the particles.

In addition to the biodegradable polyesteramides as represented by formula IV, the micro- or nanoparticles of the present invention may further comprise one or more other polymers selected from the group of biocompatible polymers.

Examples of biocompatible polymers are poly(ortho esters), poly(anhydrides), poly(D,L-lactic acid), poly(L-lactic acid), poly(glycolic acid), copolymers of poly(lactic) and glycolic acid, poly(L-lactide), poly(D,L-lactide), poly(glycolide), poly(D,L-lactide-co-glycolide), poly(L-lactide-co-glycolide), poly(phospho esters), poly(trimethylene carbonate), poly(oxa-esters), poly(oxa-amides), poly(ethylene carbonate), poly(propylene carbonate), poly(phosphoesters), poly(phosphazenes), poly(tyrosine derived carbonates), poly(tyrosine derived arylates), poly(tyrosine derived iminocarbonates), copolymers of these polymers with poly (ethylene glycol) (PEG), or combinations thereof.

In principle the micro- or nanoparticles may be prepared in a manner known in the art, provided that the polymers used in the prior art are replaced by the biodegradable polyesteramides of Formula (IV). In general particles can for example be prepared via aggregation with heat or pH adjustment, via co-acervation (phase separation), via spray drying or via solvent extraction. An overview of preparation methods has been disclosed in J. Control Release, 102:313-332, in 2005 by Freitas S et al. The micro or nanoparticles of the present invention are preferably prepared via oil in water emulsion method. This method is disclosed in detail in Example I.

If desired the micro- or nanoparticles may be loaded with one or more bioactive agents. Loading may be achieved by forming the micro- or nanoparticles in the presence of the bioactive agent or thereafter. To achieve micro- or nanoparticles with a high amount of bioactive agent, it is generally preferred to prepare the micro- or nanoparticles in the presence of the bioactive agent. In particular in the case that the bioactive agent is sensitive it is preferred to load the micro or nanoparticles after they have been formed. This can be achieved by contacting the micro- or nanoparticles with the bioactive agent and allowing the bioactive agent to diffuse into the micro- or nanoparticles and/or adhere/adsorb to the surface thereof.

In accordance with the invention it is possible to provide micro- or nanoparticles with one or more bioactive agents with satisfactory encapsulation efficiency. (i.e. the amount of bioactive agent in the particles, divided by the amount of active agent used). Depending upon the loading conditions, an efficiency of at least 20%, an efficiency of at least 50%, at least 75% or at least 90% or more is feasible.

Several types of micro- and nanoparticle structures can be prepared, these include substantially homogenous structures. However in case that more than one bioactive agent has to be released or in case that one or more functionality is needed it is preferred that the micro or nanoparticles are provided with a structure comprising an inner core and an outer shell. A core/shell structure enables more multiple mode of action for example in drug delivery of incompatible compounds or in imaging. The shell can be applied after formation of the core using a spray drier. The core and the shell may comprise the same or different polymers with different active agents. In this case it is possible to release the bioactive agents at different rates. It is also possible that the bioactive agent is only present in the core and that the shell is composed of a polymer.

The micro- or nanoparticles can also be used to fill a capsule or tube by using high pressure or may be compressed as a pellet, without substantially damaging the particles. It can also be used in injectable or spray-able form as a suspension in a free form or in an in-situ forming gel formulation. Furthermore, the micro- and nanoparticles can be incorporated in for example (rapid prototyped) scaffolds, coatings, patches, composite materials, gels, plasters or hydrogels.

The micro- or nanoparticles according to the present invention can be injected, sprayed, implanted or absorbed.

In a preferred embodiment, the particles according to the present invention are even essentially free of cryoprotectants. A cryoprotectant is a substance that protects a material, i.c.particles, from freezing damage (damage due to ice formation). Examples of cryoprotectants include a glycol, such as ethylene glycol, propylene glycol and glycerol or dimethyl sulfoxide (DMSO).

In still a further embodiment, the micro- or nanoparticles may comprise a magnetic or magnetisable core and a shell comprising the biodegradable polyesteramides. Suitable magnetic or magnetisable materials are known in the art. Such microparticles may be useful for the capability to be attracted by objects comprising metal, in particular steel, for instance an implanted object such as a graft or a stent. Such micro- or nanoparticles may further be useful for purification or for analytical purposes.

In a still further embodiment, the micro- or nanoparticles are imageable by a specific technique. Suitable imaging techniques are MRI, CT, X-ray. The imaging agent can be incorporated inside the micro- and nanoparticles or coupled onto their surface. Such micro- or nanoparticles may be useful to visualize how the particles migrate, for instance in the blood or in cells. A suitable imaging agent is for example gadolinium.

The micro- or nanoparticles comprising the polyesteramide copolymers according to the present invention can be used in the medical field especially in drug delivery in the field of management of pain, MSK, ophthalmology, cancer treatment, vaccine delivery compositions, dermatology, cardiovascular field, orthopedics, spinal, intestinal, pulmonary, nasal, or auricular field.

In a preferred embodiment, the invention provides for micro- or nanoparticles of the present invention for use as a medicament.

Besides in medical field the micro- or nanoparticles according to the invention may inter alia be used in an agricultural application. In that case the micro- or nanoparticles particles may comprise a pesticide or a plant-nutrient.

The present invention further relates to articles comprising the micro- or nanoparticles of the present invention. In another aspect, the invention provides for a device comprising micro- or nanoparticles. In the context of the present invention an article is an individual object or item or element of a class designed to serve a purpose or perform a special function and can stand alone.

In yet another preferred embodiment, the invention provides for a device comprising the article of the present invention. A device is a piece of equipment or a mechanism designed to serve a special purpose or perform a special function and can consist of more than one article (multi-article assembly).

Examples of devices include, but are not limited to catheters, stents, rods, implants.

The present invention will now be described in detail with reference to the following non limiting Figures and examples which are by way of illustration only.

FIG. 1: Hydrolytic degradation of PEA-I, PEA-III, PEA H/Bz and PLGA

Figure 2:
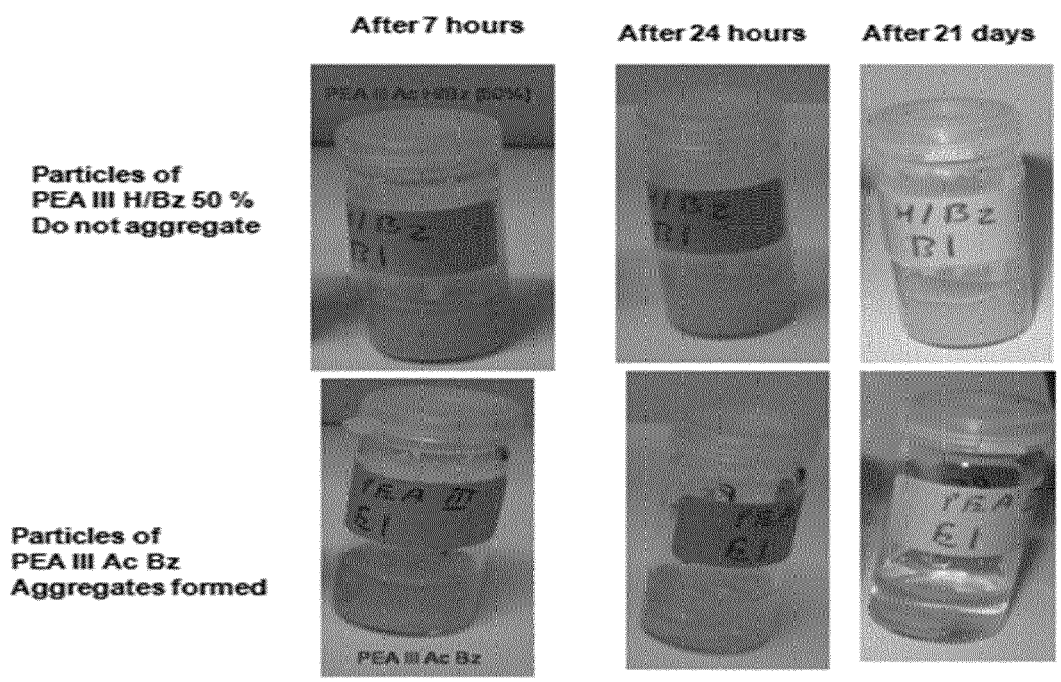

FIG. 2: Aggregation behavior of PEA-III-H/Bz compared to PEA-III-Bz.

Figure 3:
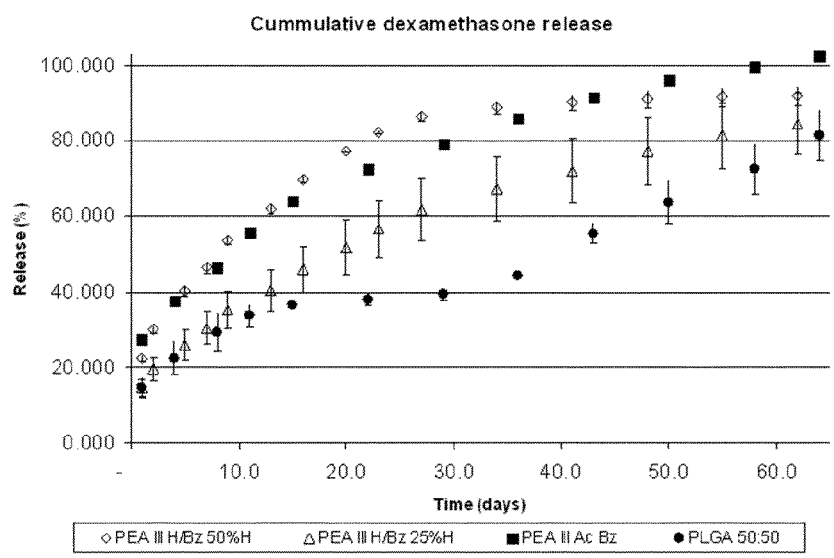

FIG. 3: Release of Dexamethasone from microparticles comprising either PEA-III-Bz; PEA-III-H/Bz 25% H; PEA-III-H/Bz 50% H or PLGA 50:50.

Figure 4:
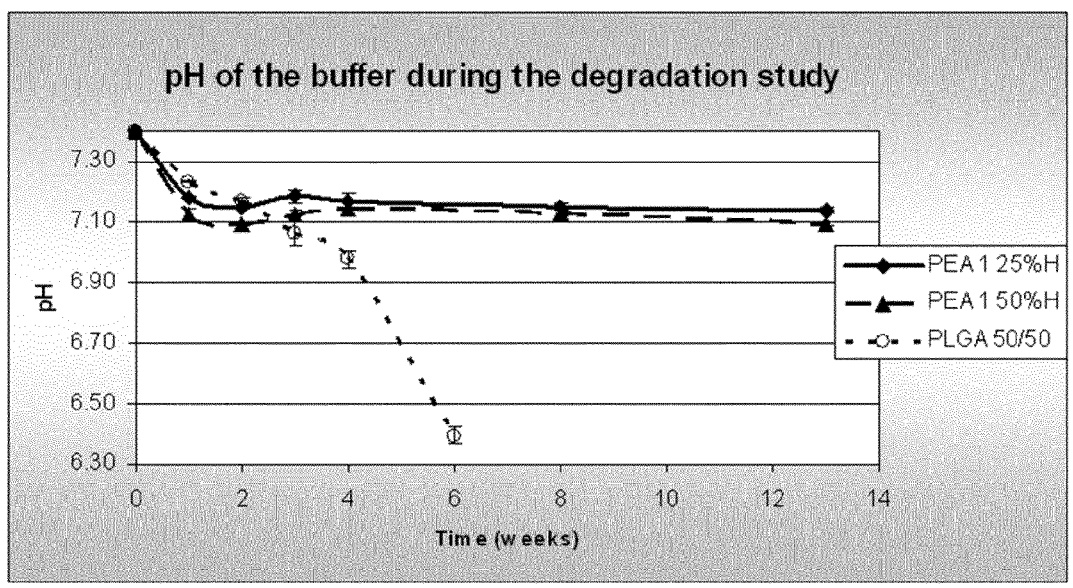

FIG. 4: pH of the buffer during the degradation study of PEA-I-H/Bz 25% H, PEA-I-H/Bz 50% H and PLGA.

FIG. 5: ARES2-rheometer with disposable geometries.

Figure 6:
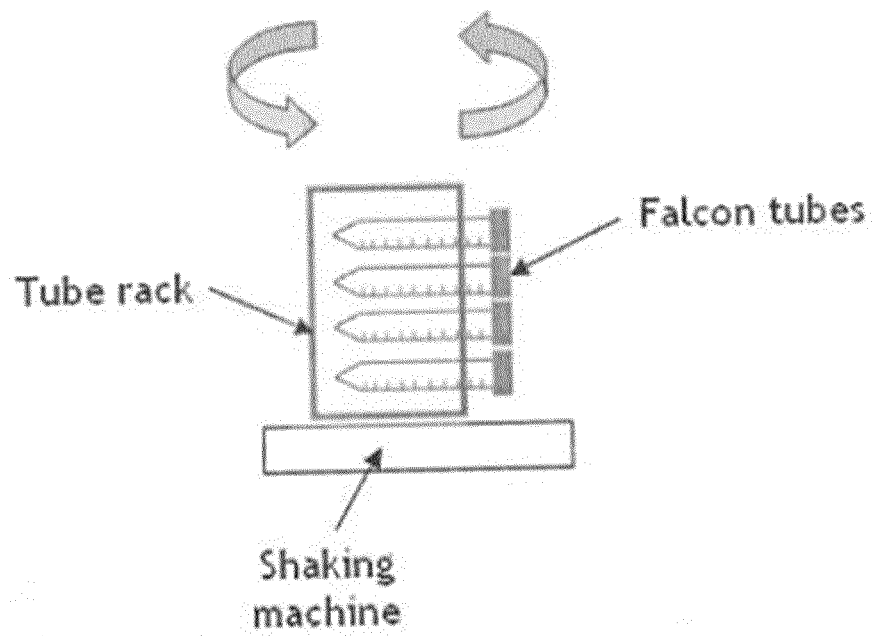

FIG. 6: Experimental set up of degradation study

EXAMPLE I

Protocol used PEA-1-Bz, copolymers of PEA-I-H/Bz 25% H, 50% H, PEA-IV-Bz, and PLGA 50/50, PLGA 75/25.

20 g oil phase comprised 5 wt % polymer, 0.5 wt % fluorescein, 9.45 wt % dimethyl sulfoxide (DMSO) and 85.05 wt % dichloromethane (DCM). Usually, 1 g of polymer was dissolved in 9 g DCM.

The water phase comprised 2.5 wt % NaCl, 1 wt % PolyVinyl Acetate (PVA) (9-10 kDa, 80% hydrolyzed) and 96.5 wt % demi water. The PVA was dissolved in warm water (80° C.) and let under stirring overnight at 75° C. The concentration used was 5% PVA in water. 200 mL of cold water phase was used per 20 g of oil phase.

For the particle formation, the water phase was poured into a 300 mL VWR beaker, 12 cm high, 6.7 cm diameter. The emulsification was done with an Ultraturrax IKA T25 coupled with a S25NK-19G stirrer. The stirring speed used was 4000 rpm. The polymer was injected via a 20 mL syringe with a bent 12 cm, 0.80 mm diameter needle. The stirring was let on 3 min after the injection end. Then the mixture was let under magnetic stirring overnight with an aluminum sheet with small holes on top of the beaker to let the solvent evaporate.

The solution used contains 0.4 mg/mL Tween 20 in water solution. Around 400 mL of washing solution was used per 20 g oil phase.

The mixture previously obtained was divided into four 50 mL falcon tubes and kept in ice. The beaker was rinsed with washing solution which was added to the tubes. They were centrifuged at 1000 rpm for 5 min. The supernatant was removed and replaced by 40 mL of washing solution. The particles were re-dispersed by gentle shaking. The tubes were centrifuged at 1000 rpm for 2 min. Once again, the supernatant was removed and replaced by 40 mL of washing solution. This washing was repeated twice and the supernatant was removed and replaced by 5 mL of washing solution. The fractions were blended into one tarred 50 mL falcon tube. The tubes were rinsed with washing solution which was added to the tarred tube.

The particles were re-dispersed (sonication bath can be used) and frozen in liquid nitrogen. At this step, the tube can be stored in a freezer. Holes were pierced in a cap which fit to the falcon tube. Then the tarred falcon tube with the pierced cap was placed in a freeze dryer (0.04 mbar, −40° C.) for at least four days.

EXAMPLE II

This study was carried out with microparticles prepared according to example I, the microparticles were loaded with fluorescein. Samples of about 25 mg of dry particles were introduced in a 15 mL flacon tube. Eighteen tubes were used per polymer studied (six data points in triple). 12 mL of 0.1 M PBS buffer, pH 7.4 with 0.05% $NaN_3$ was added to each tube. Then the tubes were placed in a tube rack under shaking in a climate chamber as represented on FIG. 6.

Then, for each data point, the pH of the buffer was measured and 2 mL of the buffer was filtered and stored in HPLC vial in a freezer.

After that, the buffer was removed and particles washed with demineralized water. The particles were then monitored by microscope and dried under vacuum at 37° C. overnight. The next step was to dissolve 5 mg of particles in 2 mL of THF to measure their molecular weight distribution.

The fluorescein loaded micro particles were challenged in the degradation study while monitoring the changes of the polymer molecular weight and particles capability to retain the loaded fluorescien. It was shown that PEA-H particles do swell quickly releasing the dye molecule. More hydrophobic PEA-Bz particles do not swell and retain the loaded fluorescien much better however the polymers do not show any sign of degradation during the experiment (13 weeks).

Results of the degradation study are shown in FIG. 1.

EXAMPLE III

W/O/W emulsion technique for preparation of PEA microparticles.

The polymers used in this study were PEA-III-Bz, PEA-III-H/Bz and PLGA.

Water 1 (W1) solution: 10 mg/ml Fitc-BSA containing 100 mg/mL trehalose .$2H_2O$ Oil composition: 5% Wt of the corresponding polymer was dissolved in chloroform. Water 2 (W2) solution: 80 gram 5% PVA and 320 gram Demiwater and 20 gram NaCl. For the fabrication of the microparticles Falcon tube (50 mL) and syringe (10 mL) were used. After adding the W1 solution to the oil, the mixture was vortexed for 30 seconds. After removing the plunger a needle was attached to the syringe the mixture was poored in the syringe (10 mL). Plunger was added when the needle of the syring was in the W2 layer. O/W mixture was added in circa 60 seconds at 4000 RPM. Mixture was stirred for additional 3 minutes at 4000 RPM. Particles were stirred overnight with magnetic stirrer and nitrogen flow.

In a stock solution of Tween 20 in H2O at 0.4 mg/mL which was prepared and stored in fridge the microparticles were suspended. Next the particle suspension was added to 4 falcon tubes. The tubes were centrifuged at 1000 rpm for 5 min and placed directly in ice. The supernatant was replaced it with 5 mL of the cold Tween 20 solution and 4 fractions were collected in a falcon tube.

The samples were re-dispersed immediately by gentle shaking and short sonication when need. Then the samples were centrifuged again and supernatant replaced. The washing procedure was repeated twice.

After a re-dispersion step the particles were immediately frozen into liquid nitrogen. Next the caps of the tubes were pierced and samples were attached to the freeze-dryer.

Approximately 20-40 mg of the freeze-dried micro particles were accurately weighted and transferred to 5 ml sample vials. Next was added two mL of stock solution to each vial containing 0.1 M PBS buffer containing 0.05 wt % $NaN_3$ and 0.05 wt % Tween 20. The vials were placed in a climate chamber at 37° C. under gentle agitation. Samples were assessed and pictures were taken after 7 and 24 hours, 3, 4, 8, 21 days. Particles of PEA-III-H/Bz 50% H were floating freely in solution in contrast with PEA-III-Bz particles which formed agglomerates already in the first in 24 hours.

Results are shown in FIG. 2.

It can be observed that micro particles consisting of PLGA 50:50 formed aggregates which could be re-dispersed after vigorous stirring. Micro particles consisting of PEA-III-Bz formed a minor amount of aggregates however the aggregates were not easy re-dispersable. Surprisingly micro particles of PEA-III-H/Bz 25% H and PEA-III-H/Bz 50% did not show agglomeration at all.

EXAMPLE IV

Micro particles were prepared via solid in oil in water (S/O/W) emulsion technique. Briefly, 100 mg dexamethasone was dispersed in 20 g $CHCl_3$ polymer solution that contained 5% polymer (oil phase). The polymers used were respectively PEA III Ac Bz, PEA III H/Bz 25% H, PEA III H/Bz 50% H and PLGA 50:50. The obtained oil phase dispersions were injected into the water phase that contained 1% PVA 9-10 kDa 88% hydrolyzed and 2.5% NaCl under ultra turrax mixing. The obtained microparticle suspension was stirred for 18 hours under ambient conditions prior to centrifugation at 1000 RPM for 5 minutes. After which the supernatant was decanted off. The microparticle residue was resuspended in 10 ml distilled water that contained 0.4 mg/ml Tween 20. The suspension was again centrifuged at 1000 RPM for 5 minutes and the supernatant was decanted off. The microparticle residue was resuspended in 10 ml distilled water that contained 0.4 mg/ml Tween 20. The obtained microparticle suspension was freeze-dried and stored at −20° C.

Dexamethasone loading was determined with 1H-NMR. Drug loading 5-7%, particle size range 10-35 μm.

Particle size was determined using SLS (Static Light Scattering).

Results are given in FIG. 3.

In duplicate approximately 20 mg freeze-dried micro particles were accurately weighted and transferred to 10 ml sample vials. To the vials 4 ml PBS buffer containing 0.05% $NaN_3$ and 0.05% Tween 20 was added. The vials were placed at 37° C. under gentle agitation. Sampling took place on a bi-weekly basis followed by a weekly sampling. During the sampling the microparticles were allowed to sediment for at least 1 hour after which 2 ml of the buffer was replaced with fresh buffer. The dexamethasone concentration was determined in the release buffer using a RP-HPLC method with DAD detection at 238 nm. The graph illustrates sustained release of dexamethasone up to 62 days from the polyesteramide matrices.

The release from PLGA followed a bimodal release curve associated with the bulk degradation property of the material. Dexamethasone release from PEA micro particles did not illustrate this behavior and showed a sustained release over the test period of 62 days. Polymers with an increasing H % exhibited increased polarity and swelling properties associated with water uptake. However surprisingly the release kinetics did not correlate with the increased H % it was anticipated that PEA-III-H/Bz 50% H would release fastest and PEA-III-Bz would release slowest.

EXAMPLE V

This study was carried out with microparticles made with the oil in water method as described in example I. 20-25 mg of microparticles was introduced in a 15 mL flacon tube. Each data point was in triple. 12 mL of PBS buffer with 0.05% $NaN_3$ was introduced to each tube. The pH was measured with a Metrohm 848 Titrino plus. The calibration was checked before each use with pH buffers of pH=7 and pH=2 or 4 and was performed with pH=2 and pH=9.

For each data point, the pH of the buffer was measured and 2 mL of the buffer was filtered and stored in HPLC vial in a freezer.

After that, the buffer was removed and particles washed with demineralized water. The particles were then monitored by microscope and dried under vacuum at 37° C. overnight. The next step was to dissolve 5 mg of particles in 2 mL of THF to measure their molecular weight distribution. Some of the polymers studied didn't dissolve in THF after being in PBS buffer lists the issues and the solutions found. Results are shown in FIG. 4.

The invention claimed is:

1. Microparticles with an average diameter of from 1 to 100 μm or nanoparticles with an average diameter of from 10 to less than 1000 nm comprising a bioactive agent and a biodegradable polyesteramide copolymer (PEA) according to the following formula:

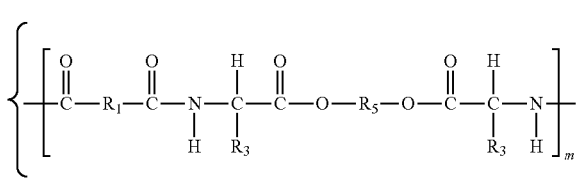

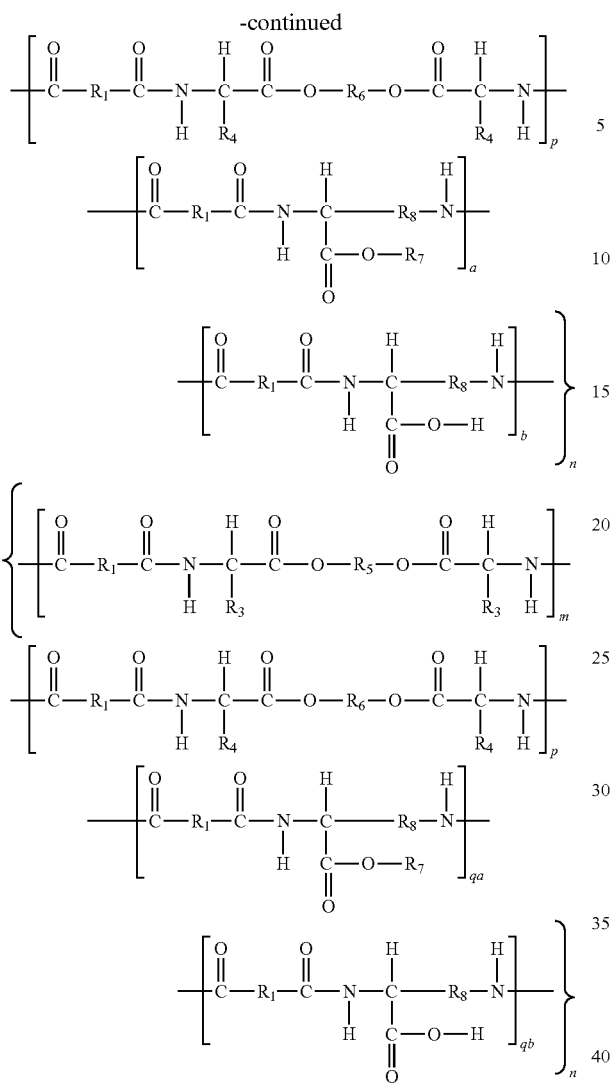

wherein
m+p is from 0.9-0.1 and q is from 0.1 to 0.9;
m+p+q=1 whereby one of m or p could be 0;
n is about 5 to about 300;
a is at least 0.05, b is at least 0.05, a+b=1, qa=q*a, and qb=q*b; wherein units of m (if present), units of p (if present), units of qa, and units of qb are all randomly distributed throughout the copolymer;
$R_1$ is independently selected from the group consisting of $(C_2-C_{20})$ alkylene, $(C_2-C_{20})$ alkenylene, —($R_9$—CO—O—$R_{10}$—O—CO—$R_9$)—, —$CHR_{11}$—O—CO—$R_{12}$—COOC$R_{11}$—, and combinations thereof;
$R_3$ and $R_4$ in a single backbone unit m or p, respectively, are independently selected from the group consisting of hydrogen, $(C_1-C_6)$alkyl, $(C_2-C_6)$alkenyl, $(C_2-C_6)$alkynyl, $(C_6-C_{10})$aryl, $(C_1-C_6)$alkyl, —$(CH_2)SH$, —$(CH_2)_2S(CH_3)$, —$CH_2OH$, —CH(OH)$CH_3$, —$(CH_2)_4NH_3+$, —$(CH_2)_3NHC(=NH_2+)NH_2$, —$CH_2COOH$, —$(CH_2)COOH$, —$CH_2$—CO—$NH_2$, —$CH_2CH_2$—CO—$NH_2$, —$CH_2CH_2COOH$, $CH_3$—$CH_2$—$CH(CH_3)$—, $(CH_3)_2$—CH—$CH_2$—, $H_2N$—$(CH_2)_4$—, Ph-$CH_2$—, $CH=C$—$CH_2$—, HO-p-Ph-$CH_2$—, $(CH_3)_2$—CH—, Ph-NH—, NH—$(CH_2)_3$—C—, NH—CH=N—CH=C—$CH_2$—;

$R_5$ is selected from the group consisting of $(C_2-C_{20})$ alkylene, $(C_2-C_{20})$alkenylene, alkyloxy or oligoethyleneglycol;
$R_6$ is selected from bicyclic-fragments of 1,4:3,6-dianhydrohexitols of structural formula (III);

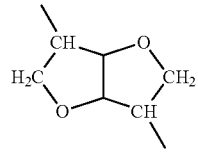

Formula III $R_7$ is selected from the group consisting of $(C_6-C_{10})$ aryl $(C_1-C_6)$alkyl;
$R_8$ is —$(CH_2)_4$—;
$R_9$ or $R_{10}$ are independently selected from $C_2-C_{12}$ alkylene or $C_2-C_{12}$ alkenylene;
$R_{11}$ or $R_{12}$ are independently selected from H, methyl, $C_2-C_{12}$ alkylene or $C_2-C_{12}$ alkenylene.

2. The microparticles or nanoparticles according to claim 1, wherein a is at least 0.5.

3. The microparticles or nanoparticles according to claim 1, wherein a is at least 0.75.

4. The microparticles or nanoparticles according to claim 1, wherein
p=0, m=0.75, and a=0.5;
wherein the m, qa, and qb units are randomly distributed;
$R_1$ is —$(CH_2)_8$—, $R_3$ is $(CH_3)_2$—CH—$CH_2$—, $R_5$ is hexyl, and $R_7$ is benzyl.

5. The microparticles or nanoparticles according to claim 1, wherein
m=0.3, p=0.45, q=0.25, and a=0.5;
wherein the m, p, qa, and qb units are randomly distributed;
$R_1$ is —$(CH_2)_8$—; $R_3$ and $R_4$ respectively, are $(CH_3)_2$—CH—$CH_2$—; $R_5$ is $(C_2-C_{20})$alkylene; and $R_7$ is benzyl.

6. The microparticles or nanoparticles according to claim 1, wherein
m=0.3, p=0.45, q=0.25, and a=0.75;
wherein the m, p, qa, and qb units are randomly distributed;
$R_1$ is —$(CH_2)_8$—; $R_4$ is $(CH_3)_2$—CH—$CH_2$—; and $R_7$ is benzyl.

7. The microparticles or nanoparticles according to claim 1, wherein
m=0.6, p=0.30, q=0.1, and a=0.5;
wherein the m, p, qa, and qb units are randomly distributed;
$R_1$ —$(CH_2)_4$—; $R_3$ and $R_4$ respectively, are $(CH_3)_2$—CH—$CH_2$—; and $R_7$ benzyl.

8. The microparticles or nanoparticles according to claim 1, wherein $R_1$ is independently selected from $(C_2-C_{20})$ alkylene.

9. The microparticles or nanoparticles according to claim 1, wherein $R_5$ is $(C_2-C_{20})$alkylene.

10. The microparticles or nanoparticles according to claim 8, wherein $R_5$ is $(C_2-C_{20})$alkylene.

11. The microparticles or nanoparticles according to claim 1, wherein the bioactive agent is a small molecule drug, or prodrug or metabolite thereof.

12. The microparticles or nanoparticles according to claim 5, wherein the bioactive agent is a small molecule drug, or prodrug or metabolite thereof.

13. The microparticles or nanoparticles according to claim 10, wherein the bioactive agent is a small molecule drug, or prodrug or metabolite thereof.

14. The microparticles or nanoparticles according to claim 1, comprising an inner core and an outer shell structure.

15. A composition comprising the microparticles or nanoparticles according to claim 11.

16. A composition comprising the microparticles or nanoparticles according to claim 12.

17. A composition comprising the microparticles or nanoparticles according to claim 13.

18. An article or device comprising the microparticles or nanoparticles according to claim 11.

19. An article or device comprising the microparticles or nanoparticles according to claim 12.

20. An article or device comprising the microparticles or nanoparticles according to claim 13.

* * * * *